United States Patent
Nelson

(10) Patent No.: US 8,734,399 B2
(45) Date of Patent: May 27, 2014

(54) SELF CLEANING CATHETER AND METHODS OF USE THEREOF

(75) Inventor: James A. Nelson, Seattle, WA (US)

(73) Assignee: Nelson Medical Devices, LLC, Seattle, WA (US)

( * ) Notice: Subject to any disclaimer, the term of this patent is extended or adjusted under 35 U.S.C. 154(b) by 1535 days.

(21) Appl. No.: 12/373,854

(22) PCT Filed: Jul. 13, 2007

(86) PCT No.: PCT/US2007/073517
§ 371 (c)(1),
(2), (4) Date: Dec. 8, 2009

(87) PCT Pub. No.: WO2008/008988
PCT Pub. Date: Jan. 17, 2008

(65) Prior Publication Data
US 2010/0106236 A1  Apr. 29, 2010

Related U.S. Application Data

(60) Provisional application No. 60/830,929, filed on Jul. 14, 2006.

(51) Int. Cl.
*A61M 5/00* (2006.01)

(52) U.S. Cl.
USPC .......................................... 604/171; 604/266

(58) Field of Classification Search
USPC ................... 604/19, 21, 73, 93.01, 171, 176, 604/263–264, 266–267, 544
See application file for complete search history.

(56) References Cited

U.S. PATENT DOCUMENTS

| 3,853,130 A | 12/1974 | Sheridan |
| 5,217,439 A | 6/1993 | McClusky |
| 5,676,688 A * | 10/1997 | Jaker et al. ..................... 606/195 |
| 5,792,114 A | 8/1998 | Fiore |
| 6,520,986 B2 | 2/2003 | Martin et al. |

FOREIGN PATENT DOCUMENTS

WO    WO 90/04430 A1    5/1990

OTHER PUBLICATIONS

European Patent Office Extended Search Report, European Application No. 07812935.0, Aug. 5, 2009, 10 pages.
European Patent Office Communication pursuant to Article 94(3) EPC, European Application No. 07812935.0, Oct. 19, 2009, 1 page.
European Patent Office, Examination Report, European Patent Application No. 07812935.0, Aug. 7, 2013, four pages.
PCT International Search Report and Written Opinion, PCT/US07/73517, Sep. 24, 2008, 7 pages.

* cited by examiner

*Primary Examiner* — Quynh-Nhu H Vu
(74) *Attorney, Agent, or Firm* — Fenwick & West LLP

(57) ABSTRACT

An improved catheter is provided for insertion into a trachea, blood vessel, bladder or urinary tract of a patient. The self cleaning catheter can be easily inserted and removed from the patient without retained, solid components falling into a patient's trachea, blood vessels, bladder, or urinary tract when the catheter is removed from the patient. The self cleaning catheter has a flexible cylindrical sleeve on the exterior of a cylindrical member that can be withdrawn to the interior of the catheter prior to removal from the patient's body. Alternatively, the catheter has a design allowing an end of the catheter to fold inward on itself prior to removal from the patient's body.

22 Claims, 8 Drawing Sheets

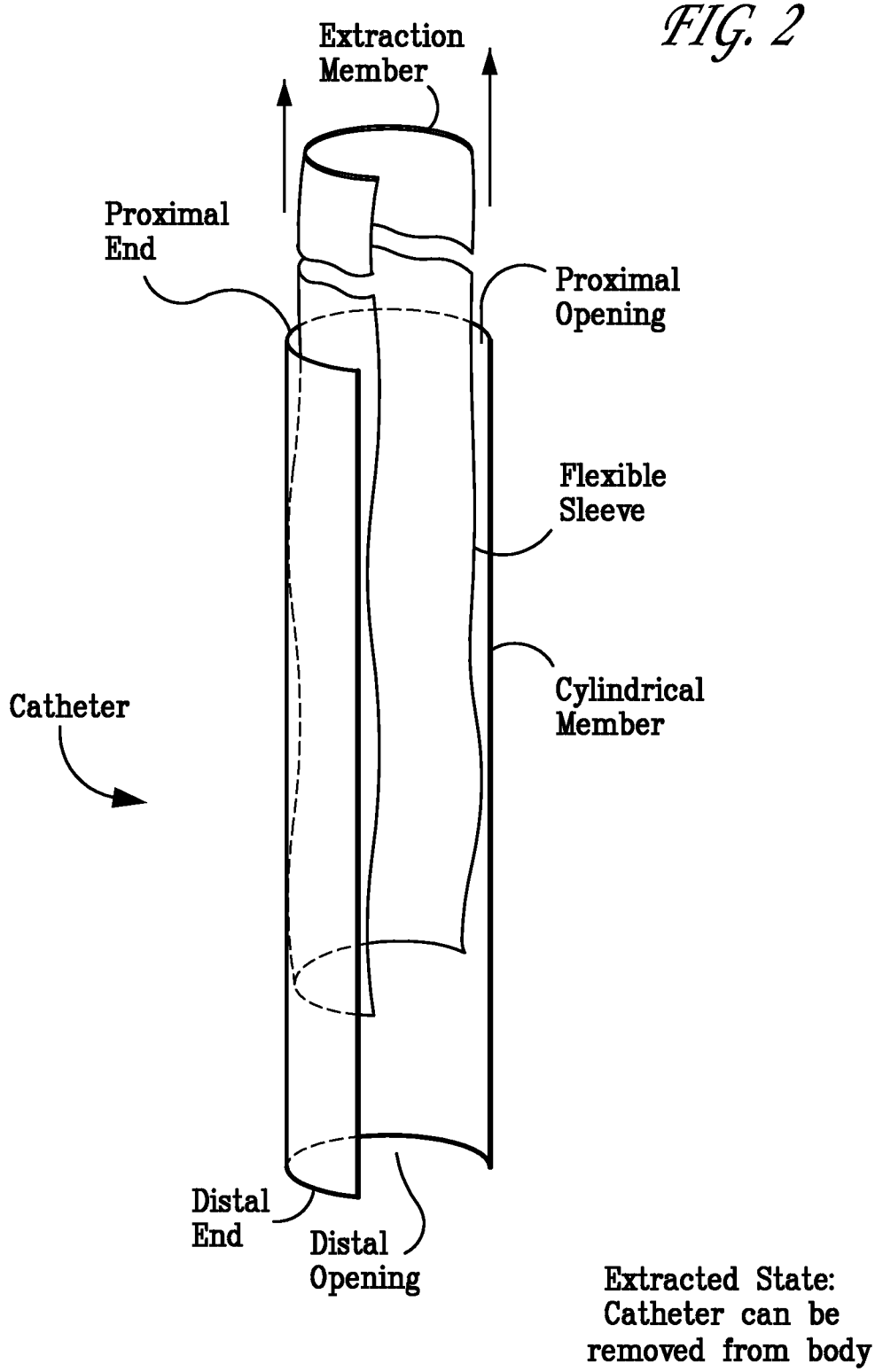

SELF CLEANING CATHETER AND METHODS OF USE THEREOF

This application is the National Stage of International Application No. PCT/US2007/073517, filed Jul. 13, 2007, and claims the benefit of the priority to U.S. Provisional Application No. 60/830,929 filed Jul. 14, 2006, both of which are incorporated by reference in their entirety.

FIELD

The present invention provides an improved catheter for insertion into a trachea, blood vessel, bladder or urinary tract of a patient. A self cleaning catheter can be easily inserted and removed from the patient without retained, solid components falling into a patient's trachea, blood vessels, bladder, or urinary tract when the catheter is removed from the patient. The self cleaning catheter can also be used to insert a stent or scaffold into the vasculature or other anatomic conduit of a patient.

BACKGROUND

When a catheter is placed through the skin into an anatomic structure, a certain amount of physiologic concretion usually is found to collect on the outer surface of the catheter during the period that it dwells in the body. In blood vessels, this concretion is usually fibrin or clot. In the bladder, urinary substances (uric acid, urea, blood-components, biofilm) coat the outer surface. In chest tubes, blood and fibrin material adhere to the outer surface. In the intestinal tract, biofilm and succus entericus or stool frequently form a cast on the outer surface of the tube. In the trachea, the outer surface of the tube gets coated with mucous and respiratory substances that form a cast or biofilm on the outer surface.

Thus, when such a catheter is removed from the body, some of this material is often "peeled" off of the catheter surface, and if the catheter passes through the body wall, much of this detritus is left within the anatomic structure that has been cannulated. When this is blood clot in a vessel, it can lead to clot formation with a venous embolus from a vein (usually harmless, but can lead to thrombophlebitis) or an arterial embolus, which can be more serious if it obstructs an artery downstream The GI tract can usually expel the retained material without difficulty. Clot or fibrin masses in the pleural space can be reabsorbed or cause pleural adhesions which are of little clinical consequence. Urinary debris can cause problems if over 3-4 mm in diameter if it cannot be passed via the ureter or urethra, and such catheter debris can act as a nidus for bladder stone formation. With a minitracheotomy tube, the debris falls off into the patient's trachea, where it can stimulate a coughing episode that can increase the morbidity in emphysema or chronic obstructive pulmonary disease (COPD) patients, who are the usual candidates for use of such a tube.

COPD is a slowly progressive disease of the airways that is characterized by a gradual loss of lung function. In the U.S., the term COPD includes chronic bronchitis, chronic obstructive bronchitis, or emphysema, or combinations of these conditions. It represents the fourth leading cause of death in the U.S. 12.1 million adults ages 25 and older reported being diagnosed with COPD in 2001. About 24 million adults have evidence of impaired lung function indicating that COPD is underdiagnosed. About 119,000 adults ages 25 and older died from COPD in 2000. While the COPD death rate for females more than doubled between 1980 and 2000, and the number of deaths for females surpassed the number for males in 2000, the overall age-adjusted death rate for COPD remained higher for males in 2000. The age-adjusted COPD death rate was about 46 percent higher in males than females and 63 percent higher in whites than blacks. COPD is the fourth leading cause of death in the U.S. and is projected to be the third leading cause of death for both males and females by the year 2020.

Physicians who would normally use a COPD minitracheostomy ventilation technique may avoid using the minitracheostomy tubes because of the problem of mucous plugs falling into the trachea and leading to severe coughing episodes which leave COPD patients breathless and can actually be life threatening. The consequences of such solid material falling into the trachea is analogous to the feeling we all get when we aspirate a small food particle or sip of fluid. This set of problems of retained, solid components falling into a patient's trachea, blood vessels, bladder or urinary tract has led to a need to redesign these catheters. A need exists in the art for a design of a minitracheostomy tube in the lungs or a catheter in the blood vessel, bladder or urinary tract that can be easily inserted and then removed from the patients on a regular biweekly basis without causing severe problem of mucous plugs falling into the trachea and leading to severe coughing episodes, or debris from the catheter devices causing further complications in the patient.

SUMMARY

The present invention provides an improved catheter for insertion into a trachea, blood vessel, bladder or urinary tract of a patient. The catheter can be easily inserted and removed from the patient without retained, solid components falling into a patient's trachea, blood vessels, bladder, or urinary tract when the catheter is removed from the patient. A self-cleaning catheter is provided which comprises a cylindrical member having a proximal end and a distal end, a flexible cylindrical sleeve having a first marginal end and a second marginal end, the sleeve surrounding an exterior of the cylindrical member, wherein the first marginal end is positioned at or near an interior of the cylindrical member and is accessible through a proximal opening at the proximal end, and the second marginal end is positioned at the exterior of the cylindrical member.

A method for retaining debris on a surface of a catheter when the catheter is removed from a patient's body is provided which comprises contacting a flexible sleeve on an exterior surface of a cylindrical member, the cylindrical member having a proximal end and a distal end, and positioning a first marginal end of the sleeve at or near an interior of the cylindrical member and a second marginal end of the sleeve on the exterior surface at the proximal end of the cylindrical member. The method can further comprise providing an extraction member connected to the first marginal end and capable of applying a radial force to the first marginal end of the sleeve when the catheter is within the patient's body and the proximal end of the cylindrical member is at an exterior surface of the patient's body, wherein the extraction member is capable of pulling the flexible sleeve through the interior of the cylindrical member from the distal end toward the proximal end of the cylindrical member.

A self-cleaning catheter is provided in another embodiment of the invention which comprises a cylindrical member having a proximal end and a distal end, and a multiplicity of rings, grooves, or scouring on an interior surface of the cylindrical member from the distal end to the proximal end of the cylindrical member. Suction can be applied to assist in retaining debris during this procedure.

A method for retaining debris on a surface of a catheter when the catheter is removed from a patient's body is provided which comprises providing an extraction member to apply a radially inward force to a distal end of the catheter toward a proximal end of the catheter, compressing a multiplicity of concentric rings, grooves, or scouring on an interior surface of the catheter, wherein the extraction member is capable of moving an exterior surface of the catheter into an interior of the catheter, and retaining the debris on the exterior surface within the interior of the catheter when the catheter is removed from the patient's body. The method can further comprise disposing the extraction member through the interior of the catheter to apply the radial force through the extraction member connected to the distal end of the catheter.

The catheter can further comprise a stent or scaffold for inserting into a vasculature, artery or vein, of a patient. A method for inserting a stent or scaffold into a vasculature of a patient's body is provided which comprises contacting the stent or scaffold on an exterior surface of a cylindrical member having a proximal end and a distal end, contacting a flexible sleeve on the stent or scaffold and the exterior surface of the cylindrical member, the flexible sleeve holding the stent or scaffold in contact with the exterior surface of the cylindrical member, and positioning a first marginal end of the sleeve at or near an interior of the cylindrical member and a second marginal end of the sleeve on the exterior surface at the proximal end of the cylindrical member, wherein the cylindrical member containing the stent or scaffold and the flexible sleeve is capable of inserting into the vasculature of the patient's body. The method can further comprise providing an extraction member capable of applying a radial force to the first marginal end of the flexible sleeve, wherein the extraction member is capable of pulling the flexible sleeve through the interior from the distal end toward the proximal end of the cylindrical member, and retracting the flexible sleeve from the exterior of the cylindrical member and releasing the stent or scaffold into the vasculature of the patient's body. Small stents, which can pass through the inner lumen of the catheter, are already in use in clinical practice. This embodiment of the catheter of the present invention would be most useful for placement of stents or scaffolds which are large enough that they would be easier to place on the outside of the catheter rather than being pushed up the inner lumen when inserting the stent into the vasculature of the patient's body.

BRIEF DESCRIPTION OF THE DRAWINGS

FIG. 2 shows an embodiment of the self cleaning catheter wherein the flexible sleeve covers the exterior and part of the interior of the cylindrical member. The extraction member pulls the sleeve out through the interior of the cylindrical member. The flexible sleeve and the cylinder member are shown in a cutaway view.

DETAILED DESCRIPTION

Figure 1A:
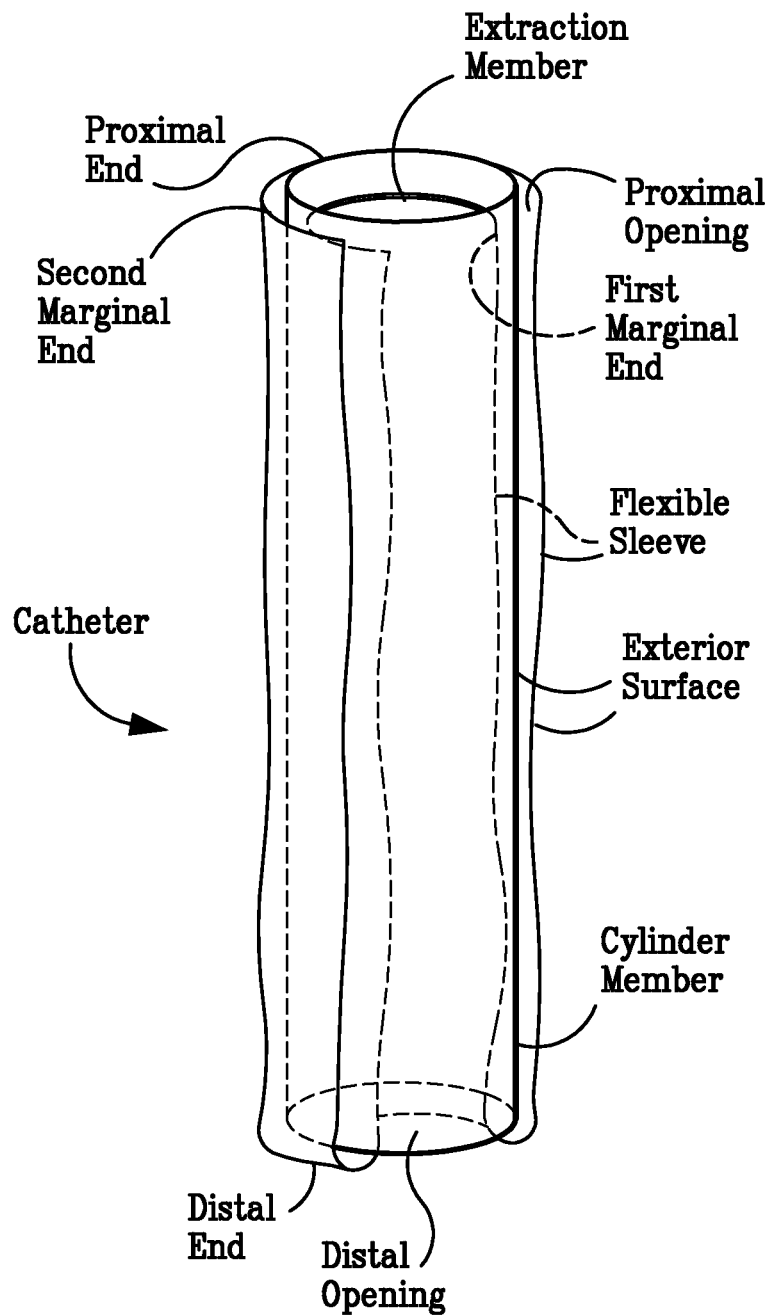
FIG. 1A shows an embodiment of the self cleaning catheter wherein the flexible sleeve covers the exterior and interior of the cylindrical member. The extraction member pulls the sleeve out through the interior of the cylindrical member. The flexible sleeve is shown in a cutaway view.

The present invention provides a self cleaning catheter for insertion into a trachea, blood vessel, bladder or urinary tract of a patient. The patient is a mammalian subject, e.g., a human subject. The catheter can be easily inserted and removed from the patient without retained, solid components falling into a patient's trachea, blood vessels, bladder, or urinary tract when the catheter is removed from the patient. The present invention provides a catheter, for example, a minitracheostomy device, vascular catheter, or urinary catheter. For example, a minitracheostomy tube that will be constructed in such a way that, while it can be placed into the trachea using the traditional, minimally invasive Seldinger technique, it will retract within itself (somewhat like turning a coat sleeve inside out) with enough ease and capacity to allow the coated tracheal secretions to be retained within the collapsed, inverted tubing. If the outer coating can be trapped by this mechanism, the tube could be used more often and more easily, since the coughing episodes could be eliminated. In another design embodiment, the self cleaning catheter can comprise a cylindrical inner guide member and a flexible sleeve constructed of a durable tubular membrane that covers the cylindrical inner guide member. The flexible sleeve surrounds the exterior of the cylindrical member and the sleeve is accessible through the interior of the cylindrical member.

The present invention provides a minitracheostomy device, vascular catheter, or urinary catheter that is a tapered tube. In one embodiment of the self cleaning catheter, an inner guide catheter is shaped and sized appropriately for a minitracheostomy device or catheter. A flexible sleeve is a durable, tubular membrane that can be pushed down through the inside of the catheter and then pulled over the outside of the catheter to act as both the inner and outer surface of the assembly. The inner portion of the flexible sleeve or tubular membrane can then be fastened to a detachable fitting for the $O_2$ tubing. The membrane covers the outside of the catheter and wraps around the distal end of the catheter to a position inside the catheter where the membrane is attached to an extraction member. After the assembly had been in use for the appropriate time, the tubular membrane can be detached and the entire tubular membrane extracted through the inside of the catheter, trapping outer debris as it is pulled through. Suction on the $O_2$ fitting can be used to further remove debris during this action. A new assembly can then be placed.

In another embodiment, the present invention provides a minitracheostomy device that is a tapered minitracheostomy tube that would be scoured with circular rings, grooves, or scouring on the inside, but would be smooth on the outside, and that would appear nearly identical in function and appearance to the existing catheters now used for this purpose. The portion of the tube actually inside the trachea would be analogous to existing catheters. However, after the tube had been in place for the usual period of time (10-14 days) and required changing for placement of a new, clean tube, the self cleaning catheter would allow the tube to be withdrawn by inverting it, facilitated by its construction, into itself so that no foreign material would fall into the trachea.

The catheter or minitracheostomy device can be constructed of materials known in the art of catheters or tracheostomy devices. Catheters can be constructed of materials including, but not limited to, polyethylene, polypropylene, polyurethane, polyvinyl chloride, or Teflon®. The cylindrical member will have enough rigidity to maintain the shape and function of a typical minitracheostomy catheter, for example, a silicon tube construct. A coating material forming the flexible sleeve will have properties that require it to be thin, strong, and "slippery." It should also be easy to liquefy to facilitate the coating of the cylindrical member in order to form the final structure of the self-cleaning catheter or the catheter to deliver a stent. The flexible sleeve must slip off the cylindrical member easily and be strong and durable enough that it not fragment upon withdrawal. For example, Teflon® may be a good choice for the flexible sleeve, but other materials capable of gliding on the cylindrical member may also be used.

The removal technique would be designed to be atraumatic and relatively simple. A retrieval device—a wire balloon, small metallic expandable ball, rubber or plastic balloon catheter, or hook mechanism, would be designed to reach the distal end of the catheter. When the distal tip is engaged by the extractor, traction would be used to invert the tube into itself for removal. Another possible technique would be to construct a thin thread or wire removal system into the wall of the catheter which would allow the catheter to be inverted upon itself with retraction on the thread or wire assembly. In another aspect, the flexible sleeve/tubular membrane is engaged by the extractor, and the flexible sleeve is pulled off the exterior of the catheter and into the interior of the catheter. To increase the effectiveness of the catheter, the device could be constructed with a drug eluting material to reduce bacterial growth and biofilm formation.

Since this new tube would eliminate the most common adverse side effect of the minitracheostomy tubes in current use, this invention would allow expanded utilization of minitracheostomy technology to a larger number of patients. With elimination of "peeling" the catheter coating off into the windpipe, a major side effect of the minitracheostomy technique could be eliminated.

Although the minitracheostomy, as it is currently used, is often chosen for cosmetic reasons (the oxygen tubing can be kept beneath one's shirt, and the tracheal catheter concealed by the collar) there are other benefits to the patient that might argue for its use once the complication of foreign material into the trachea on withdrawal is eliminated. The minitracheostomy technique, with placement into the trachea beneath the vocal chords, allows normal speaking, coughing, and respiration. Administration of oxygen via a minitracheostomy tube reduces respiratory "dead space", and allows the oxygen delivery system to be triggered by normal subglottic respiratory pressure changes during a normal respiratory cycle.

The minitracheostomy device, as described in detail herein, will lead to improved respiratory therapy for large numbers of COPD and emphysema patients, as well as patients requiring supplemental oxygen because of muscle weakness. In other embodiments, the self cleaning catheter can be a vascular catheter, or a urinary catheter.

The vascular catheter can be designed to deliver a stent or scaffold to the vasculature, artery or vein, of a patient. In one aspect, placement of the stent in the vasculature of the patient is achieved in circumstances where the stent is too large to fit within the inner lumen of a reasonably sized catheter. In this embodiment, the stent is placed on the outside of the catheter to deliver the stent to the vasculature. This method of placing the stent will improve delivery of the stent to an artery or vein of the patient.

The description of specific embodiments for carrying out the present invention are offered for illustrative purposes only, and are not intended to limit the scope of the present invention in any way.

DETAILED DESCRIPTION OF FIGURES

The self cleaning catheter is useful for a number of applications including, but not limited to a tracheostomy tube, a minitracheostomy tube, a vascular catheter, or a urinary catheter. The tracheostomy tube, urinary catheter or vascular catheter may have a distal end within the patient's body and a proximal end outside the patient's body. The vascular catheter may have both proximal and distal ends within the patient's body with control of the catheter occurring from the proximal end. The vascular catheter can be used to hold a stent or scaffold which is inserted and released into a desired location in the vasculature of the patient.

Figure 1B:
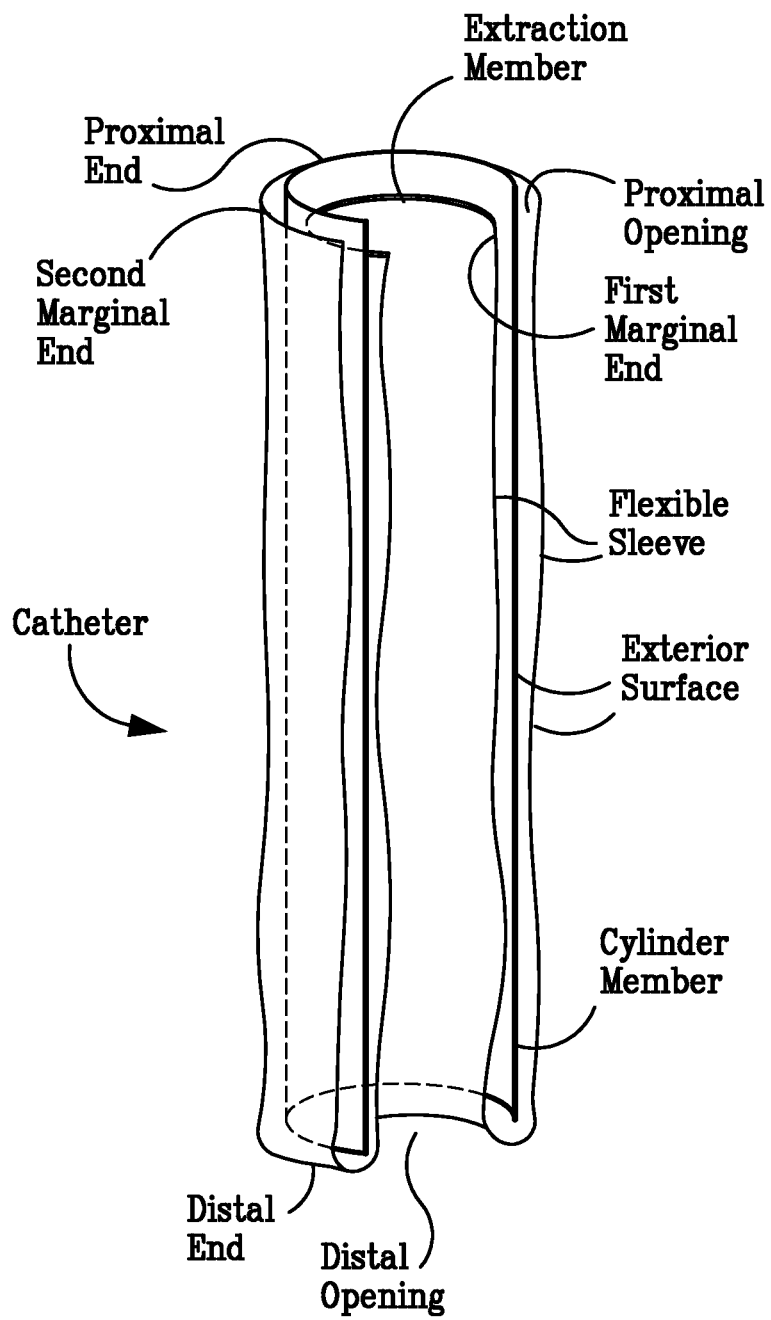
FIG. 1B shows an embodiment of the self cleaning catheter wherein the flexible sleeve covers the exterior and interior of the cylindrical member. The extraction member pulls the sleeve out through the interior of the cylindrical member. The flexible sleeve and the cylinder member are shown in a cutaway view.

FIGS. 1A and 1B shows an embodiment of the self cleaning catheter. The catheter comprises a cylindrical member having a proximal end and a distal end, a proximal opening at the proximal end and a distal opening at the distal end. A flexible sleeve is cylindrical and surrounds the cylindrical member covering essentially the entire exterior surface of the cylindrical member and a portion of the interior surface of the cylindrical member. The flexible cylindrical sleeve has a first marginal end and a second marginal end. The first marginal end is located at an interior surface of the cylindrical member. The second marginal end is located on the exterior surface of the cylindrical member near the proximal end. The flexible sleeve is attached to the extraction member. The flexible sleeve surrounds the exterior surface of the cylindrical member. The flexible sleeve continuously surrounds the interior of the cylindrical member, an edge of the distal end, and the exterior of the cylindrical member. In FIG. 1A, the flexible sleeve is shown in a cutaway view. In FIG. 1B, the flexible sleeve and the cylinder member are shown in a cutaway view.

As shown in FIG. 2, the extraction member can be withdrawn through the proximal opening at the proximal end thereby applying a radial force on the first marginal end of the flexible sleeve. The force pulls the flexible sleeve down the exterior of the cylindrical member, over an edge at the distal end, through the distal opening at the distal end and into the interior of the cylindrical member. At this point, the surface debris on the flexible sleeve is contained within the interior of the cylindrical member. The catheter can now be removed from the body without depositing debris within the body, for example, keeping the trachea and lungs free from debris. The flexible sleeve and the cylinder member are shown in a cutaway view.

FIGS. 1 and 2 show the extraction member near the proximal end of the cylindrical member. The extraction member may have a Luerlok® connection to an air supply for tracheal tubes or other fluid supply for vascular catheters.

Figure 3:
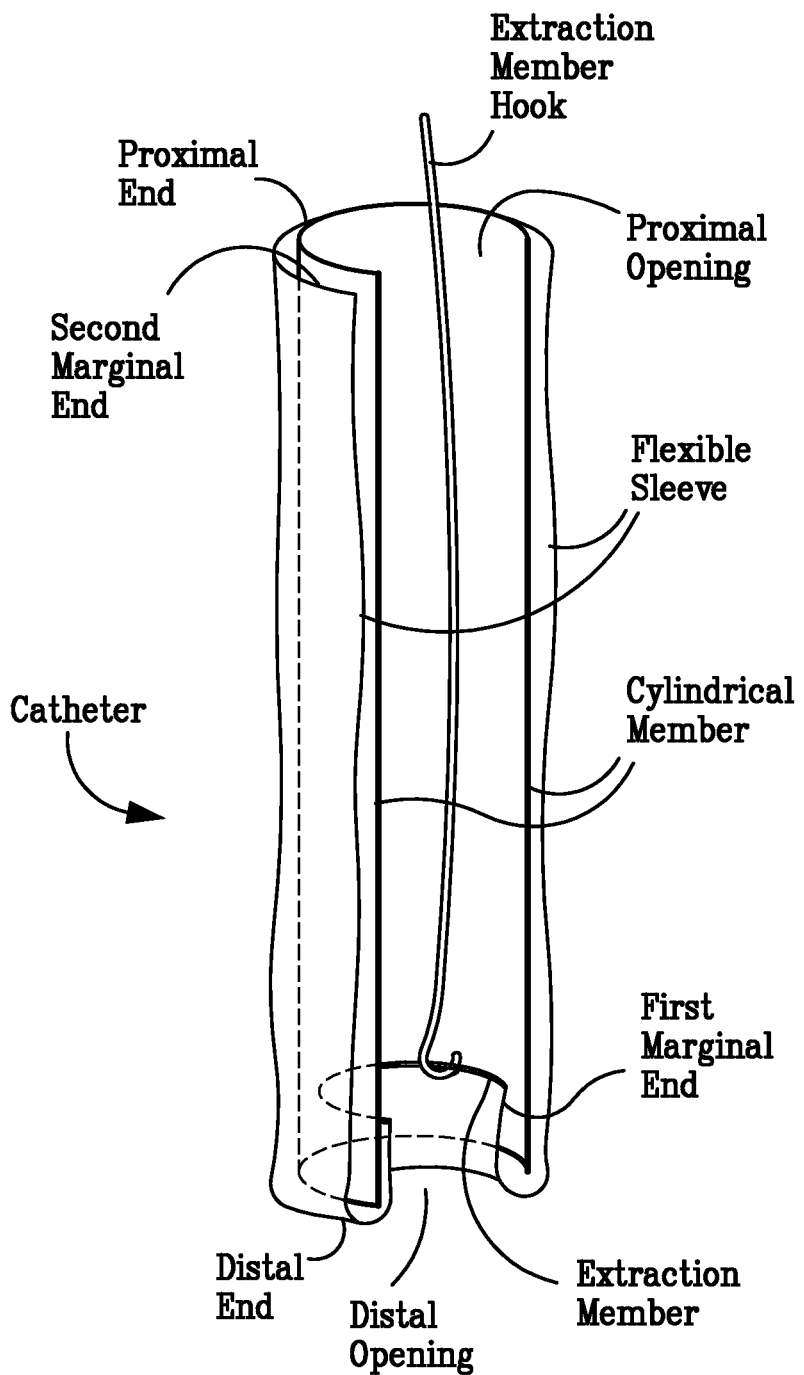
FIG. 3 shows the embodiments of FIG. 1 or 2 after the sleeve has been extracted to a position within the cylindrical member wherein the catheter can be removed from the patient's body. The flexible sleeve and the cylinder member are shown in a cutaway view.

FIG. 3 is a variation of the design of FIGS. 1 and 2. The extraction member is located within the interior of the cylindrical member and closer to the distal end. The extraction member is attached to the first marginal end of the flexible sleeve. Similarly to the embodiment in FIGS. 1 and 2, the extraction member can be withdrawn through the interior and through the proximal opening at the proximal end of the cylindrical member thereby applying a radial force on the first marginal end of the flexible sleeve. The force pulls the flexible sleeve down the exterior of the cylindrical member, over the edge at the distal end, through the distal opening and into the interior of the cylindrical member. At this point, the surface debris on the flexible sleeve is contained within the interior of the cylindrical member. The catheter can now be removed from the body without depositing debris within the body, for example, keeping the trachea and lungs free from debris. The flexible sleeve and the cylinder member are shown in a cutaway view.

Figure 4:
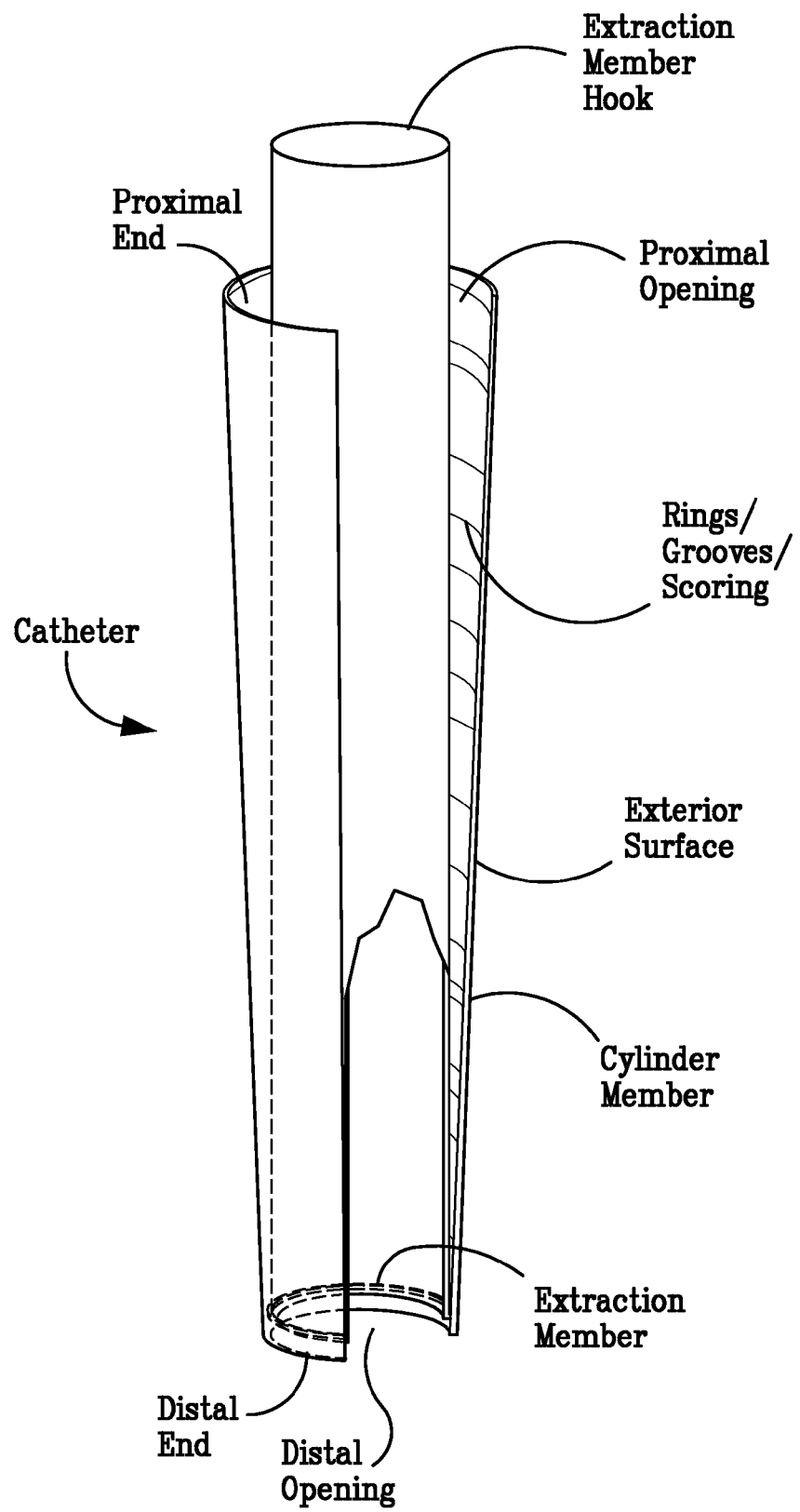
FIG. 4 shows an embodiment of the self cleaning catheter wherein the cylindrical member has rings, grooves or scoring on the interior surface which allow the cylindrical member to fold into the interior of the cylinder upon extraction with the extraction member. The cylinder member and the extraction member hook are shown in a cutaway view.
Figure 5:
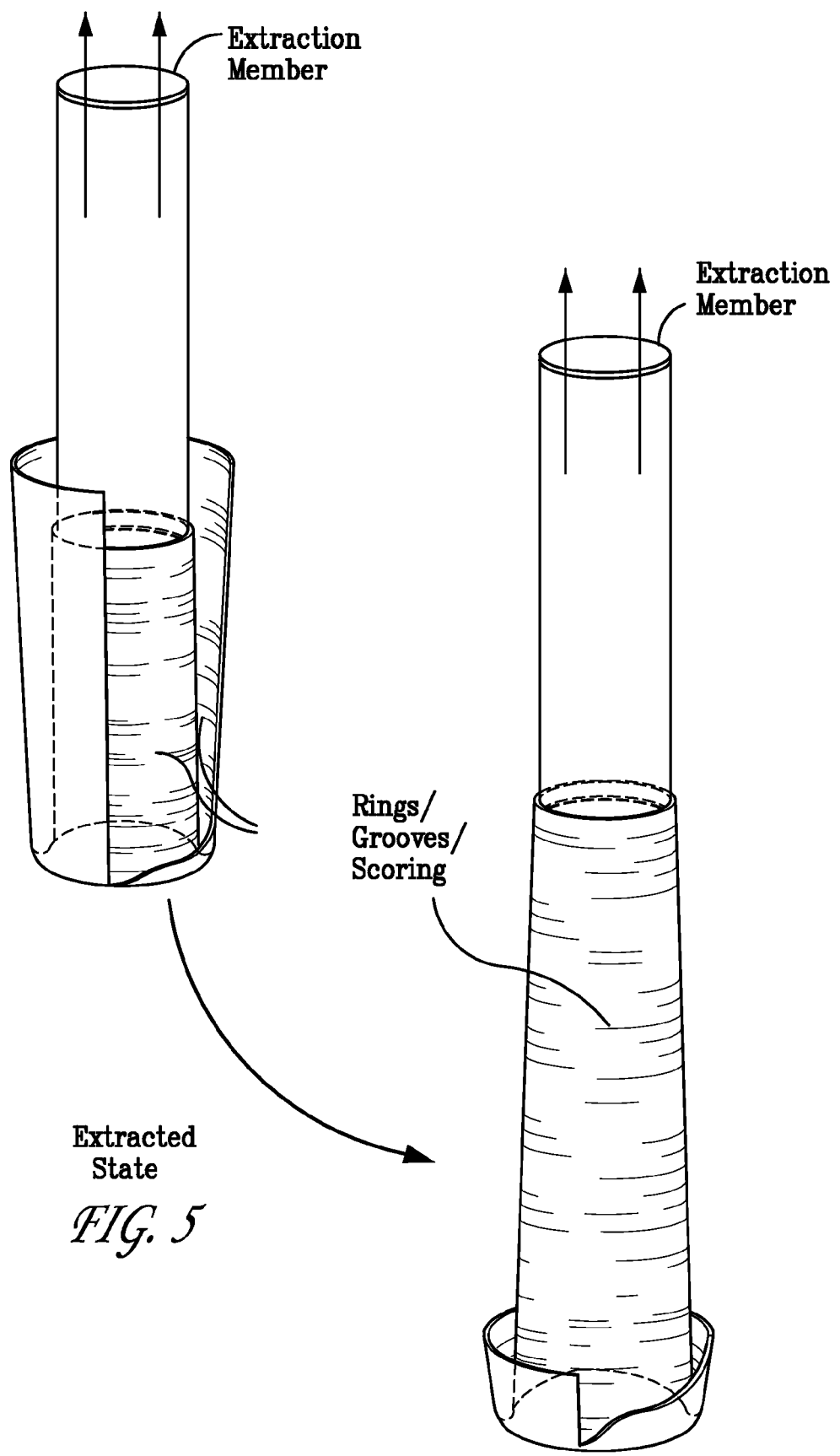
FIG. 5 shows the embodiment of FIG. 4 after the cylindrical member has been retracted to a position wherein the catheter can be removed from the patient's body. The cylinder member and the extraction member hook are shown in a cutaway view.

FIGS. 4 and 5 show an alternative embodiment of the self-cleaning catheter. FIG. 4 shows a catheter comprising a cylindrical member having a proximal end and a distal end, and a proximal opening at the proximal end and a distal opening at the distal end. The cylindrical member has a series of rings, grooves, or scoring on the interior of the cylindrical member allowing the cylindrical member to fold into itself beginning at the distal end, as shown in FIG. 5. In one aspect, the cylindrical member can be slightly tapered from the proximal end toward the distal end. An extraction member is attached at the distal end of the cylindrical member. An extraction member hook or extension is attached to the extraction member and applies a radial inward force at the distal end causing the cylindrical member to fold into the interior of the cylindrical member. Any debris accumulated on the exterior of the cylindrical member will be drawn into the interior space and trapped there when the catheter is removed from the patient's body. See FIG. 5. The cylinder member and the extraction member hook are shown in a cutaway view.

Figure 6:
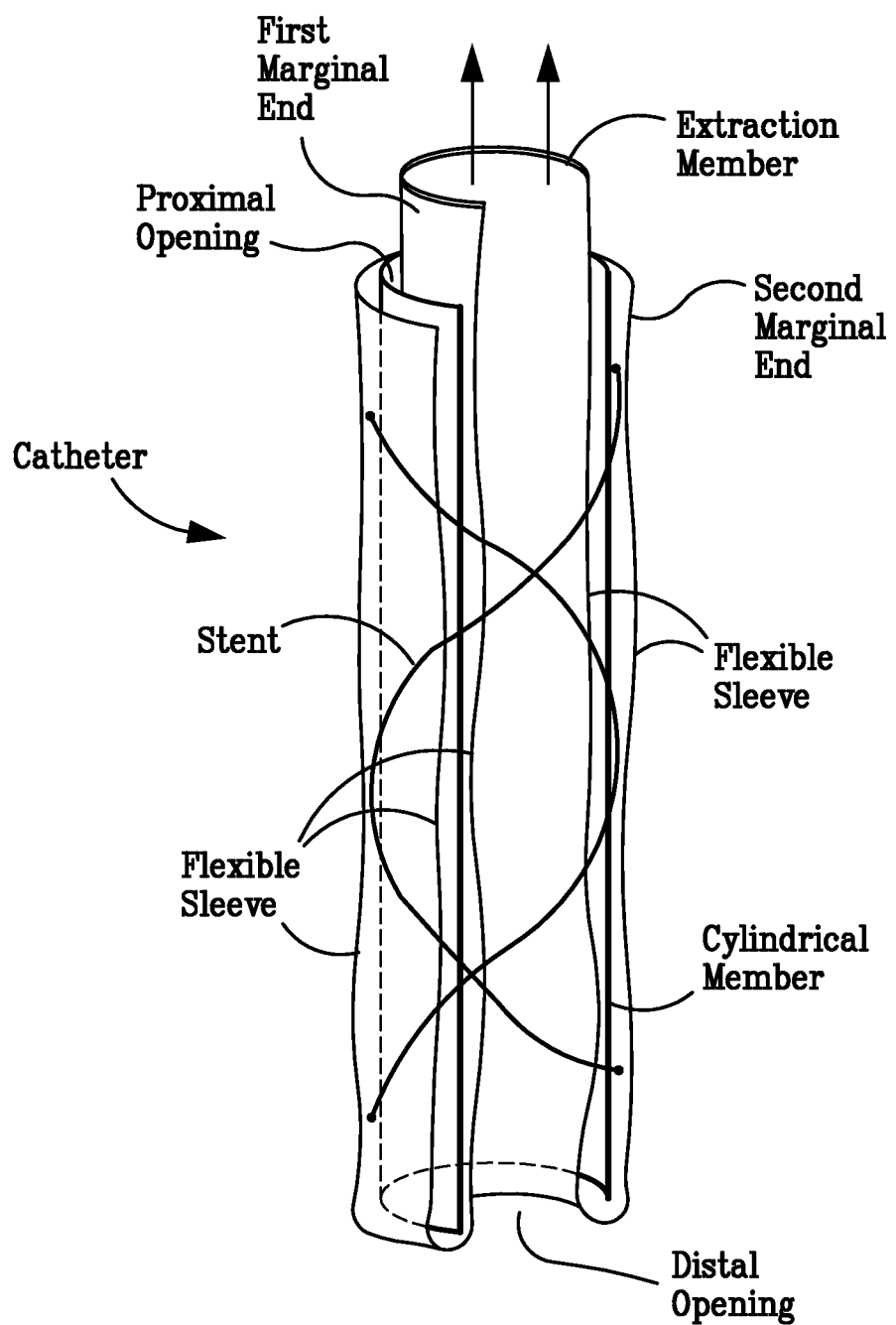
FIG. 6 shows an embodiment of the self cleaning catheter capable of delivering an expandable stent or scaffold to the vasculature of a patient. The flexible sleeve and the cylinder member are shown in a cutaway view.
Figure 7:
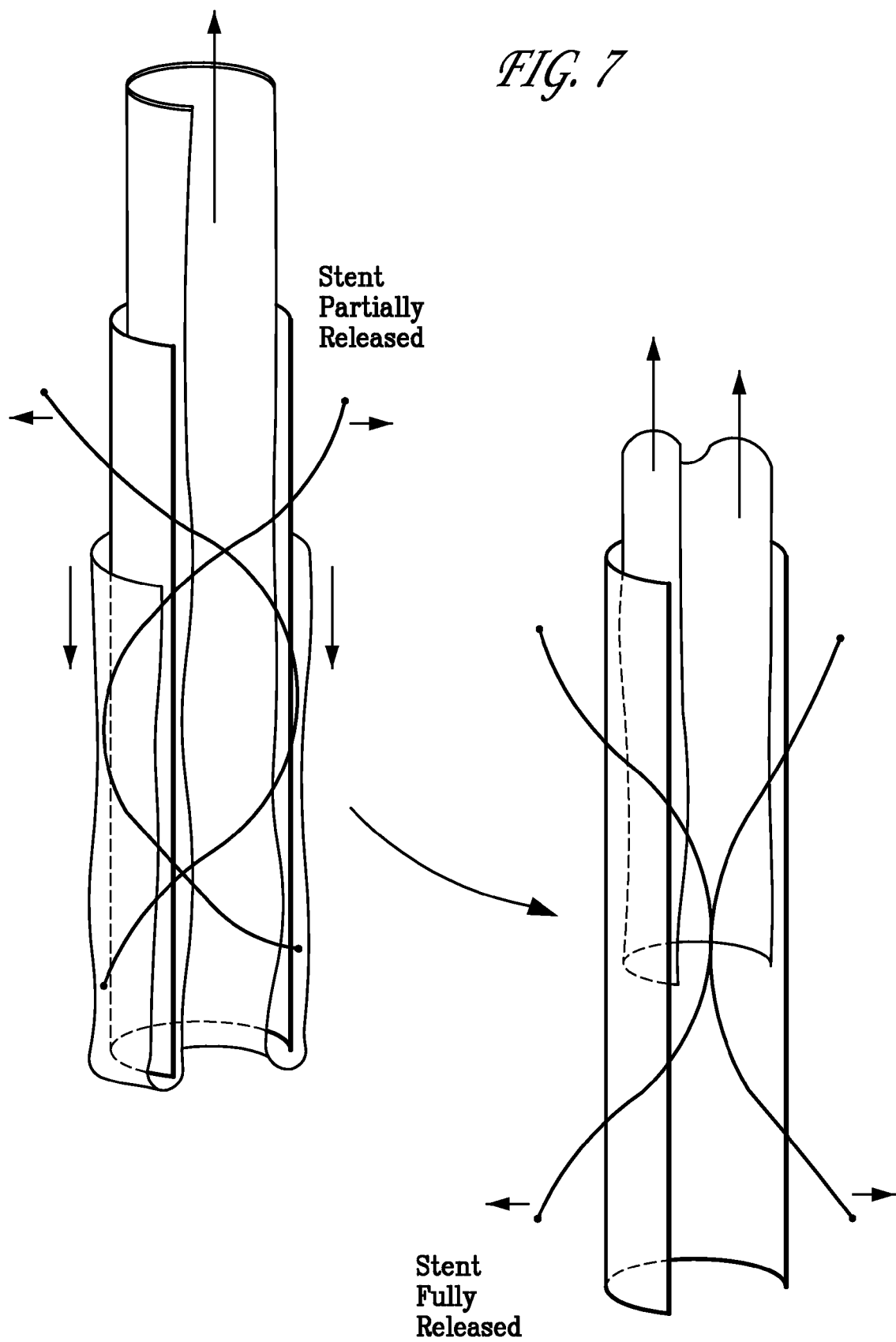
FIG. 7 shows the release of the expandable stent or scaffold from the catheter. The flexible sleeve and the cylinder member are shown in a cutaway view.

FIGS. 6 and 7 show a catheter capable of delivering a stent or scaffold to the vasculature of a patient. The stent or scaffold is expandable into the vasculature, artery or vein, of the patient. The catheter comprises a cylindrical member having a proximal end and a distal end. The stent or scaffold surrounds the exterior surface of the cylindrical member and is substantially in contact with the cylindrical member, as shown in FIG. 6. For different shapes of stents or scaffolds, the cylindrical member can be designed to hold the stent or scaffold on the exterior surface of the cylindrical member. When the stent or scaffold is released from the catheter, it will expand to fit the vasculature of the patient, as shown in FIG. 7. The stent or scaffold is held in contact with the exterior surface of the cylindrical member by a flexible sleeve that covers the exterior surface of the cylindrical member. The flexible sleeve is cylindrical and surrounds the cylindrical member covering essentially the entire exterior surface of the cylindrical member and a portion of the interior surface of the cylindrical member. The flexible tubular sleeve has a first marginal end and a second marginal end. The first marginal end is located at an interior surface of the cylindrical member. The second marginal end is located on the exterior surface of the cylindrical member near the proximal opening. The flexible sleeve is attached to an extraction member. The flexible sleeve continuously surrounds the interior of the cylindrical member, an edge of the distal end, and the exterior of the cylindrical member. The flexible sleeve and the cylinder member are shown in a cutaway view.

As shown in FIG. 7, the stent or scaffold is released from the catheter, when the extraction member is withdrawn through the proximal opening at the proximal end thereby applying a radial force on the first marginal end of the flexible sleeve. The force pulls the flexible sleeve down the exterior of the cylindrical member, over an edge at the distal end, through the distal opening, and into the interior of the cylindrical member. As the flexible sleeve is withdrawn, the sleeve releases the stent or scaffold structure from the cylindrical member. The structure can then expand to fit the vasculature of the patient. In addition to releasing the stent or scaffold, the catheter can be removed from the body without depositing debris within the body, for example, keeping the vasculature free from blood clots.

The disclosures of each patent, patent application and publication cited or described in this document are hereby incorporated herein by reference, in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

What is claimed is:

1. A self-cleaning catheter comprising,
   a cylindrical member having a proximal end and a distal end, and
   a flexible cylindrical sleeve having a first marginal end and a second marginal end, the sleeve surrounding an exterior of the cylindrical member, wherein the first marginal end is positioned at or near an interior of the cylindrical member, and the second marginal end is positioned at the exterior of the cylindrical member, wherein the flexible sleeve covers a length of the exterior of the cylindrical member from the proximal end to the distal end of the cylindrical member and continuously surrounds the interior of the cylindrical member, an edge of the distal end, and the exterior of the cylindrical member; and the first marginal end is positioned at an interior of the cylindrical member.

2. The catheter of claim 1 further comprising:
   the cylindrical member having the proximal end capable of remaining outside a patient's body and the distal end capable of inserting within the patient's body; and
   a suction device attached to the proximal end of the cylindrical member.

3. The catheter of claim 1 wherein the first marginal end of the flexible sleeve is positioned at an interior of the distal or proximal end of the cylindrical member.

4. The catheter of claim 1 further comprising an extraction member movably attached at the first marginal end through the interior of the cylindrical member, wherein the extraction member is accessible through an opening in the proximal end of the cylindrical member.

5. The catheter of claim 4 wherein the extraction member is a tubing lock mechanism positioned at the proximal end and is attached to the first marginal end.

6. The catheter of claim 4 wherein the extraction member is a wire balloon, small metallic expandable ball, rubber or plastic balloon catheter, or hook.

7. The catheter of claim 1 wherein the catheter is a tracheostomy tube, a minitracheostomy tube, a vascular catheter, or a urinary catheter.

8. The catheter of claim 1, further comprising,
a multiplicity of rings, grooves, or scouring on an interior surface of the cylindrical member from the distal end to the proximal end of the cylindrical member.

9. The catheter of claim 8, further comprising:
the cylindrical member having the proximal end capable of remaining outside a patient's body and the distal end capable of inserting within the patient's body; and
a suction device attached to the proximal end of the cylindrical member.

10. The catheter of claim 8 further comprising:
an extraction member disposed within an interior of the cylindrical member and movably attached to the distal end of the cylindrical member,
wherein the extraction member is a wire balloon, small metallic expandable ball, rubber or plastic balloon catheter, or hook and is accessible through an opening in the proximal end of the cylindrical member.

11. A method for retaining debris on a surface of a catheter when the catheter is removed from a patient's body comprising,
contacting a flexible sleeve on an exterior surface of a cylindrical member, the cylindrical member having a proximal end and a distal end;
positioning a first marginal end of the sleeve at or near an interior of the cylindrical member and a second marginal end of the sleeve on the exterior surface at the proximal end of the cylindrical member; and
providing an extraction member connected to the first marginal end and capable of applying a radial force to the first marginal end of the sleeve when the catheter is within the patient's body and the proximal end of the cylindrical member is at an exterior surface of the patient's body,
wherein the extraction member is capable of pulling the flexible sleeve through the interior of the cylindrical member from the distal end toward the proximal end of the cylindrical member.

12. The method of claim 11 further comprising:
providing an extraction member capable of extracting the flexible sleeve through the interior of the cylindrical member and outside the patient's body; and
providing a suction device connected at the proximal end of the cylindrical member during removal from the patient's body.

13. The method of claim 12, wherein:
the extraction member is capable of pulling the sleeve through the interior of the cylindrical member toward the proximal end and retaining the debris on the surface of the sleeve within the interior of the cylindrical member when the catheter is removed from the patient's body;
the extraction member is accessible through an opening in the proximal end of the cylindrical member; and
the extraction member is positioned at the proximal end and is attached to the first marginal end.

14. The method of claim 13 wherein the extraction member is a tubing lock mechanism at the proximal end of the catheter.

15. The method of claim 13 wherein the extraction member is a wire balloon, small metallic expandable ball, rubber or plastic balloon catheter, or hook mechanism.

16. The method of claim 11 further comprising:
covering with the flexible sleeve a length of the exterior surface from the proximal end to the distal end of the cylindrical member; and
covering with the flexible sleeve a continuous area surrounding the interior of the cylindrical member, an edge of the distal end and the exterior of the cylindrical member, wherein the first marginal end is positioned at the interior of the cylindrical member.

17. The method of claim 16 wherein the first marginal end of the flexible sleeve is at the interior of the distal or proximal end of the cylindrical member.

18. The method of claim 11 wherein the catheter is a tracheostomy tube, a minitracheostomy tube, a vascular catheter, or a urinary catheter.

19. The method of claim 11, further comprising:
providing an extraction member to apply a radially inward force to a distal end of the catheter toward a proximal end of the catheter, compressing a multiplicity of concentric rings, grooves, or scouring on an interior surface of the catheter;
wherein the extraction member is capable of moving an exterior surface of the catheter into an interior of the catheter, and retaining the debris on the exterior surface within the interior of the catheter when the catheter is removed from the patient's body; and
providing a suction device connected at the proximal end of the cylindrical member during removal from the patient's body.

20. The method of claim 19 further comprising:
disposing the extraction member through the interior of the catheter to apply the radial force through the extraction member connected to the distal end of the catheter;
wherein the extraction member is capable of moving toward the proximal end of the catheter and applying the radial force on the distal end toward the interior of the catheter and toward the proximal end.

21. The method of claim 20 wherein the extraction member is a wire balloon, small metallic expandable ball, rubber or plastic balloon catheter, or hook mechanism.

22. The method of claim 20 wherein the extraction member is accessible through an opening in the proximal end of the cylindrical member.

* * * * *